United States Patent [19]

Nohira et al.

[11] Patent Number: 5,371,282

[45] Date of Patent: Dec. 6, 1994

[54] PROCESS FOR OPTICAL RESOLUTION OF (+)-CIS-4-AMINOCYCLOPENT-2-EN-1-CARBOXYLIC ACID DERIVATIVE

[75] Inventors: Hiroyuki Nohira, Saitama; Kojiro Hara; Kensuke Nagashima, both of Tokyo; Tatsuhiko Hayashibara, Niigata, all of Japan

[73] Assignee: Kuraray Co., Ltd., Kurashiki, Japan

[21] Appl. No.: 128,110

[22] Filed: Sep. 29, 1993

[30] Foreign Application Priority Data

Oct. 2, 1992 [JP] Japan .................. 4-289632

[51] Int. Cl.$^5$ .............................................. C07B 55/00
[52] U.S. Cl. ................................................... 562/401
[58] Field of Search .......................................... 562/401

[56] References Cited

U.S. PATENT DOCUMENTS

| | | | |
|---|---|---|---|
| 4,845,272 | 7/1989 | Nohira et al. | 562/401 |
| 4,904,822 | 2/1990 | Nohira et al. | 562/401 |
| 5,066,826 | 11/1991 | Nohira et al. | 560/60 |
| 5,235,095 | 8/1993 | Kadkhodayan | 562/401 |
| 5,235,101 | 8/1993 | Patil et al. | 562/401 |

FOREIGN PATENT DOCUMENTS

| | | |
|---|---|---|
| 567940 | 12/1958 | Canada . |
| 683725 | 4/1964 | Canada . |
| 2048286 | 2/1992 | Canada . |
| 508133 | 10/1992 | European Pat. Off. . |
| 5092343 | 12/1980 | Japan . |
| 680217 | 7/1992 | Switzerland . |

OTHER PUBLICATIONS

European Journal of Medicinal Chemistry, vol. 24, No. 4, 1989, pp. 415–420, M. Ikbal, "Synthese des Deux Enantiomeres de l'Analogue Carbocyclique du Nicotamide Ribose et Evaluation de Leurs Proprietes Biologiques".

Journal of Chem. Soc., Chem. Commun., 1990, pp. 1120–1121, Steven J. C. Taylor, et al., "Chemoenzymatic Synthesis of (−)-Carbovir Utilizing a Whole Cell Catalysed Resolution of 2-Azabicyclo[2.2.1]hept-5-en-3-one".

Journal of Chem. Soc. Perkins Trans. 1, 1991, pp. 2479–2484, Martin F. Jones, et al., "Total Synthesis of (−)-Carbovir".

Journal of Chem. Soc. Perkins Trans. 1, 1991, pp. 2605–2607, Stanley M. Roberts, et al., "Enzymatic Resolution of cis- and trans-4-Hydroxycyclopent-2-Enylmethanol Derivatives and a Novel Preparation of Carbocyclic 2′,3′-Dideoxydidehydronucleosides and Aristeromycin".

Journal of Chem. Soc. Perkin Trans. 1, 1992, pp. 589–592, Chris T. Evans, et al., "Potential Use of Carbocyclic Nucleosides for the Treatment of AIDS: Chemo-Enzymatic Synthesis of the Enantiomers of Carbovir".

*Primary Examiner*—Paul J. Killos
*Attorney, Agent, or Firm*—Oblon, Spivak, McClelland, Maier & Neustadt

[57] ABSTRACT

In optical resolution of an optically inactive (±)-cis-4-aminocyclopent-2-en-1-carboxylic acid derivative into its (+)-derivative and (−)-derivative, the (±)-cis-4-aminocyclopent-2-en-1-carboxylic acid derivative is allowed to react with an optically active cis-2-(arylalkylamino)cyclohexanemethanol or optically active α-alkylbenzylamine serving as an optically resolving agent, to form diastereomer salts corresponding to the (+)-cis-4-aminocyclopent-2-en-1-carboxylic acid derivative and the (−)-cis-4-aminocyclopent-2-en-1-carboxylic acid derivative.

4 Claims, No Drawings

PROCESS FOR OPTICAL RESOLUTION OF (+)-CIS-4-AMINOCYCLOPENT-2-EN-1-CARBOXYLIC ACID DERIVATIVE

BACKGROUND OF THE INVENTION

1. Field of the Invention

This invention relates to a process for the optical resolution of an optically inactive (±)-cis-4-aminocyclopent-2-en-1-carboxylic acid represented by Formula (1) (hereinafter abbreviated "(±)ACP acid") into its optically active (+)ACP acid derivative and (−)ACP acid derivative.

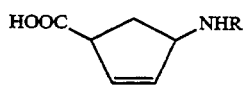

wherein R represents an acyl group.

2. Description of the Related Art

In recent years, there is a world-wide problem of an increase in persons infected with AIDS (aquired immune deficiency syndrome) viruses, and it has been attempted to remedy AIDS infections by various methods. Under such circumstances, an optically active isomer of a compound commonly called a carbovir, represented by Formula (2):

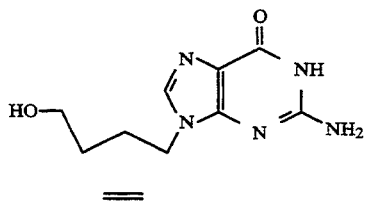

has attracted notice because of its inhibitory action against the proliferation of AIDS viruses.

Thus, it is attempted to synthesize the optically active carbovir of Formula (2). For example, it is proposed to use a chiral natural product, aristeromycin, as a starting material (C. Willamson, A. M. Exall et al., Poster Presentation at SCI Medical Chemistry Symposium, Cambridge, 1989). This method, however, has the problem that the chiral natural product as a starting material is available with so great a difficulty and is so expensive that the carbovir can not be produced in an industrial scale and at a low cost.

For this reason, it is attempted to chemically synthesize the carbovir of Formula (2) without using as a starting material the natural product available with difficulty (J. Chem. Soc., Chem. Commun., 1120(1990); J. Chem. Soc., Perkin Trans., 1, 2479(1990); and J. Chem. Soc., Perkin Trans., 1, 589(1992). An important subject in the chemical synthesis of such a carbovir is for one thing how an optically active (−)-4-hydroxymethyl-2cyclopentenyl group is introduced into the main skeleton of the carbovir of Formula (2).

As one of conventional reliable means for settling this subject, it is proposed to use a synthesis method in which optically active (−)-4-N-acetylamino-1-hydroxymethyl-2-cyclopentene of Formula (3) which is a compound corresponding to the (−)-4-hydroxymethyl-2-cyclopentenyl group is allowed to react with 2-amino-4,6-dichloropyridine of Formula (4) to produce (−)-4-hydroxymethyl-4-[(2'-amino-6'-chloropyrimidin-4'-yl)amino]-2-cyclopentene of Formula (5), as shown below [J. Chem. Soc., Chem. Commun., 1120(1990)].

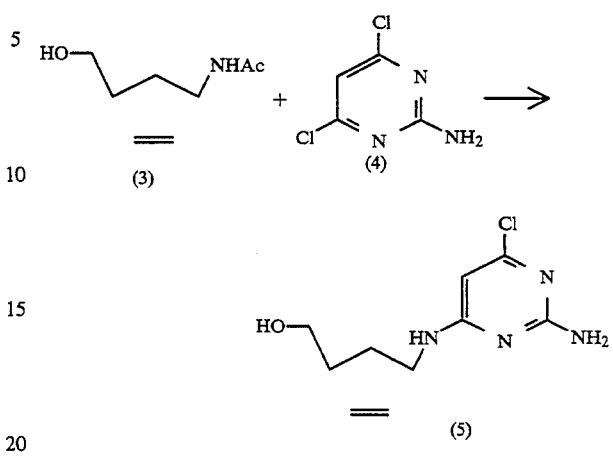

In this case, the compound of Formula (3) is synthesized by subjecting optically inactive 2-azabicyclo[2.2.1]hept-5-en-3-one to optical resolution in the presence of a whole cell catalyst to obtain optically active (−)-2-azabicyclo[2.2.1]hept-5-en-3-one, subjecting this isomer to hydrolysis to obtain an optically active ACP acid as an intermediate material and further subjecting this acid to esterification reaction, acetylation reaction and reduction reaction.

However, the method making use of the whole cell catalyst as mentioned above requires a reasonably long time for the optical resolution in order to obtain the optically active ACP acid, and has been involved in the problem that it is not suited for large-scale treatment and the compound can not be produced in an industrial scale and at a low cost.

SUMMARY OF THE INVENTION

This invention intends to solve the problems involved in the prior art discussed above, and an object thereof is to make it possible to produce in a high purity, in a high yield and in an industrial scale, the optically active ACP acid useful as a starting material for synthesizing the carbovir.

The present inventors have discovered that the above object can be achieved when an optically active cis-2-(arylalkylamino)cyclohexanemethanol or an optically active α-alkylbenzylamine is made to act on an optically inactive (±)ACP acid derivative, as an optically resolving agent. They have thus accomplished the present invention.

The present invention provides a process for optically resolving a (±)ACP acid derivative represented by Formula (1):

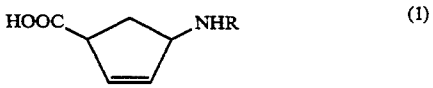

wherein R represents an acyl group; into its (+)ACP acid derivative and (−)ACP acid derivative, wherein the process comprises the step of allowing the (±)ACP acid derivative to react with an optically resolving agent comprising an optically active cis-2-(arylalkylamino)cyclohexanemethanol or an optically active α-alkylbenzylamine, to form diastereomer salts respectively corresponding to said (+)ACP acid derivative and said (−)ACP acid derivative.

DETAILED DESCRIPTION OF THE INVENTION

The optical resolution process of the present invention will be described below in detail.

In the present invention, a (±)ACP acid derivative is allowed to react with an optically active cis-2(arylalkylamino)cyclohexanemethanol, i.e., (+)- or (−)-cis-2-(arylalkylamino)cyclohexanemethanol, or an optically active α-alkylbenzylamine, i.e., (+)- or (−)-α-alkylbenzylamine, which is an amine compound serving as an optically resolving agent, to form diastereomer salts respectively corresponding to the (+)ACP acid derivative and the (−)ACP acid derivative. In this case, the diastereomer salts are formed by dissolving, with heating, the optically resolving agent in the (±)ACP acid derivative preferably in the presence of a solvent.

The acyl group of the substituent R in the (±)ACP acid derivative of Formula (1), used in the present invention can be exemplified by an alkanoyl group such as an acetyl group or a propionyl group, an aroyl group such as a benzoyl group or a naphthoyl group, and a heteroaroyl group such as a franoyl group. These may also be optionally substituted with other substituent.

The (±)ACP acid derivative of Formula (1) can be produced by subjecting (±)-2-azabicyclo[2.2.1]hept-5-en-3-one to hydrolysis according to a conventional method, for example, by heating it in an aqueous dilute hydrochloric acid solution to form (+)ACP acid, followed by acylation of the amino group to convert it into an amido group.

In the present invention, there are no particular limitations on the molar ratio of the optically active cis-2-(arylalkylamino)cyclohexanemethanol or optically active α-alkylbenzylamine used as an optically resolving agent, to the (±)ACP acid derivative. In order to resolve the (±)ACP acid derivative in a good efficiency and a high purity, it is preferable to use the optically active resolving agent in an equivalent mole of from 0.4 to 1.0 based on the (±)ACP acid derivative.

The arylalkyl group in the optically active cis-2-(arylalkylamino)cyclohexanemethanol and the alkyl group in the optically active α-alkylbenzylamine may be selected from various groups capable of resolving the (±)ACP acid derivative. The arylalkyl group may preferably be a benzyl group, and the alkyl group may preferably be a methyl group.

Such an optically active resolving agent and the (±)ACP acid derivative may preferably be allowed to react in the presence of a solvent, as previously mentioned. Such a solvent can be exemplified by water; $C_{1-6}$, preferably $C_{1-4}$, alkanols such as methanol, ethanol, 2-propanol, 1-propanol and 1-butanol; $C_{3-6}$ alkyl methyl ketones such as acetone and methyl isobutyl ketone; cyclic ethers such as dioxane, tetrahydrofuran and tetrahydropyran; mixtures of any of these; benzenes unsubstituted or substituted with methyl or the like lower alkyl, such as benzene, toluene and xylene; $C_{6-8}$ cycloalkanes such as cyclohexane; and $C_{6-10}$ alkanes such as n-hexane, n-octane and n-decane. In particular, in view of the advantage that a highly pure, optically active ACP acid derivative can be obtained, it is preferable to use water or 2-propanol as the solvent. Especially when water is used as the solvent, a more highly pure, optically active ACP acid derivative can be obtained by neutralizing an excess (±)ACP acid derivative present in the reaction mixture after the formation of diastereomer salts, by the use of a base such as sodium hydroxide, potassium hydroxide, lithium hydroxide or ammonia.

The amount of the solvent used may vary depending on the type of the solvent, dissolving temperature and crystallization temperature. In usual instances, the solvent may preferably be used in an amount of from about 150 to 2,000 ml per mol of the optically active resolving agent used.

The resulting diastereomer salts are two kinds of ammonium carboxylates different from each other, formed of substituted amino groups pertaining to the optically resolving agent and carboxyl groups pertaining to the ACP acid. When the optically resolving agent used is a (+)-isomer, a [(+)ACP acid derivative.(+)optically resolving agent] salt and a [(−)ACP acid derivative.(+)optically resolving agent] salt are obtained correspondingly to the (+)ACP acid derivative and the (−)ACP acid derivative, respectively. When the optically resolving agent used is a (−)-isomer, a [(+)ACP acid derivative.(−)optically resolving agent] salt and a [(−)ACP acid derivative. (−)optically resolving agent] salt are obtained.

The diastereomer salts obtained in this way can be mutually optically resolved by conventional methods. For example, the diastereomer salts can be separated by utilizing a difference in their solubility to solvents. In this case, the reaction solution may preferably be cooled to a given crystallization temperature into a supersaturated state so that one diastereomer salt which is more sparingly soluble can be preferentially crystallized from the reaction solution in which the diastereomer salts are formed. A preferable crystallization temperature may very depending on the amount of the solvent, the type of the solvent and the solvent temperature. From an economical viewpoint, it may usually be in the range of from −10 to 50° C.

When one diastereomer salt is crystallized, a very small amount of crystals of the diastereomer salt to be crystallized may preferably be added to the reaction solution as seed crystals. The diastereomer salt thus deposited can be isolated by a commonly available method such as filtration or centrifugal separation.

The diastereomer salts having been optically resolved in this way can be formed into optically active ACP acid derivatives by conventional methods. For example, the diastereomer salts are each hydrolyzed using an alkali hydroxide to convert the carboxyl group of an ACP acid derivative into an alkali metal salt, during which the amine compound optically resolving agent is released. The released compound is removed by extraction with ether and a mineral acid such as hydrochloric acid or sulfuric acid is made to act on the aqueous layer, whereby the optically active (+)ACP acid derivative or (−)ACP acid derivative can be produced.

The optically resolving agent recovered by the extraction with ether may be reused.

As described above, in the process for the optical resolution of the (±)ACP acid derivative according to the present invention, the optically active amino compound cis-2-(arylalkylamino)cyclohexanemethanol or optically active α-alkylbenzylamine and the (±)ACP acid derivative are allowed to react to form the diastereomer salts corresponding to the (+)ACP acid derivative and the (−)ACP acid derivative. Hence, for example, it becomes possible to preferentially deposit one diastereomer salt, utilizing a difference in solubility to solvents, of the diastereomer salts different from each other. Thus, according to the present invention, the (+)- or (−)-cis-4-aminocyclopent-2-en-1-carboxylic acid with a high optical purity, useful as a starting material for synthesizing the carbovir having an inhibitory action against the proliferation of AIDS viruses, can be readily separated from a mixture of these.

EXAMPLES

In the following, production of the (+)ACP acid derivative to which the optical resolution process of the present invention is applied will be illustrated as Reference Examples, and the present invention will be further described in detail by giving Examples.

Reference Example 1

Synthesis of (±)ACP acid {(±)-cis-4-aminocyclopent-2-en-1-carboxylic acid}

To 4.58 g (42 mmol) of (±)-2-azabicyclo[2.2.1]hept-5-en-3-one, 190 ml of 1N hydrochloric acid was added, and the mixture was refluxed for 2 hours with heating. The solvent was evaporated, and the resulting white crystals were washed with 30 ml of acetone, followed by drying to give 6.59 g of crude crystals of the subject (+)ACP acid. This crude crystals were dissolved in ethanol (20 ml) with heating, and thereafter ethyl acetate (85 ml) was added to the resulting solution, followed by cooling to room temperature. The crystals thus deposited were filtrated to give 4.26 g (25.7 mmol; yield: 61.2%) of the subject (+)ACP acid (melting point: 169–172° C.).

Reference Example 2

Synthesis of (±)ACP acid derivative-A {(±)-cis-4-benzamidocyclopent-2-en-1-carboxylic acid}

To 8 ml of water, the (±)ACP acid (1.64 g, 10.0 mmol) obtained in Reference Example 1 was added, and an aqueous solution prepared by dissolving sodium hydroxide (0.976 g, 24.4 mmol) in water (5 ml) was further added under ice cooling, followed by stirring. To the resulting reaction solution, a solution prepared by dissolving benzoyl chloride (1.83 g, 1.30 mmol) in dioxane (10 ml) and an aqueous solution prepared by dissolving sodium hydroxide (0.511 g, 13.8 mmol) in water (5 ml) were simultaneously dropwise added over a period of 25 minutes. After the addition was completed, stirring was continued at 0° C. for 3 hours. Thereafter, the reaction solution was washed twice with ethyl acetate (30 ml), and then 4N hydrochloric acid (4 ml) was further added to make the solution acidic. A white precipitate thereby deposited was filtrated, followed by washing with water and then drying to obtain 2.12 g of crude crystals of the subject (±)ACP acid derivative A. To this crude crystals, acetonitrile (34 ml) was added to dissolve them with heating, followed by cooling to room temperature. Crystals deposited were filtrated to give 1.91 g (8.20 mmol; yield: 81.9%) of needle crystals of the subject (±)ACP acid derivative-A (melting point: 170–172° C.).

Example 1

Optical resolution (1) of (±)ACP acid derivative-A

To methanol (110 ml), the (±)ACP acid derivative-A (4.51 g, 19.4 mmol) obtained in Reference Example 2 and (+)-cis-2-(benzylamino)cyclohexanemethanol (4.25 g, 19.4 mmol) as an optically resolving agent were added. While these were heated and reacted, the solvent was evaporated. To the resulting yellow oil, 2-propanol (28 ml) was added to dissolve them with heating, followed by cooling to room temperature. Crystals deposited were filtrated, and the resulting crystals were further recrystallized four times with 2-propanol. The diastereomer salt crystals thus obtained had the properties as shown below. Melting point: 133–134° C. $[\alpha]_{589} -10.7°$ (c=1.042, methanol)

As a result, the diastereomer salt crystals obtained were found to be a [(−)ACP acid derivative-A.(+)optically resolving agent] salt.

To the crystals obtained, an aqueous 1N sodium hydroxide solution (8 ml) was added, and the optically resolving agent released was separated and removed by extraction with the addition of diethyl ether (15 ml). To the aqueous layer formed, 4N hydrochloric acid was added, and a white precipitate thereby deposited was filtrated to give 1.08 g (4.64 mmol) of (−)ACP acid derivative-A {(−)-cis-4-benzamidocyclopent-2-en-1-carboxylic acid (yield: 47.8% based on (+)ACP acid derivative-A; $[\alpha]_{589} -24.0°$ (c =1.049, methanol); melting point: 150.0–151.1° C.).

The (−)ACP acid derivative-A thus obtained was allowed to react with optically active 1-(1naphthyl)ethylamine to derive its amido form, which was then analyzed by HPLC to reveal that it had an optical purity of 99% or more.

Conditions for HPLC
Column: Inertsil SIL (5 μm in diameter)
Mobile phase: n-Hexane/2-propanol=95/5
Flow rate: 1.0 ml/min.

Example 2

Optical resolution (2) of (±)ACP acid derivative-A

To water (40 g), the (±)ACP acid derivative-A (10.0 g, 43.3 mmol) obtained in Reference Example 2, (+)-α-methylbenzylamine (2.62 g, 21.6 mmol)as an optically resolving agent and an aqueous 20% sodium hydroxide solution (4.3 g, 21.5 mmol) were added to dissolve them with heating. Thereafter, the reaction solution was slowly cooled to 5° C. Crystals deposited were filtrated to obtain 3.90 g of crystals of diastereomer salts (yield: 51.2% based on (+)ACP acid derivative).

To 3.00 g of the crystals obtained, 33 ml of an aqueous 1N sodium hydroxide solution was added to release the optically resolving agent. The optically resolving agent was separated and removed by adding thereto 33 ml of diethyl ether. To the remaining aqueous layer, 4N hydrochloric acid was added, and a white precipitate thereby deposited was filtrated to give 1.82 g of (+)ACP acid derivative-A {(−)-cis-4-benzamidocyclopent-2-en-1carboxylic acid} (yield: 92.5% based on diastereomer salts. The $[\alpha]_{589}$ of the (+)ACP acid derivative-A obtained was 24.0° (c=1.021, methanol). This value was coincident with the absolute value of the specific rotation of the (−)ACP acid derivative-A obtained in Example 1. From this fact, the optical purity was found to be 99% or more.

Reference Example 3

Synthesis of (±)ACP acid derivative-B {(±)-cis-4-(N-carbobenzoxy)cyclopent-2-en-1-carboxylic acid}

To water (10 ml), the (±)ACP acid (2.46 g, 15.0 mmol) obtained in Reference Example 2 was added, and an aqueous solution prepared by dissolving sodium hydroxide (1.47 g, 36.8 mmol) in water (7 ml) was further added under ice cooling, followed by stirring. To the resulting solution, a toluene solution containing 30% by weight of carbobenzoxychloride and an aqueous solution prepared by dissolving sodium hydroxide (0.830 g, 20.8 mmol) in water (7 ml) were simultaneously dropwise added over a period of 25 minutes. After the addition was completed, stirring was further continued at 0° C. for 3 hours. Thereafter, the reaction solution was washed twice for extraction with diethyl ether (30 ml), and then 2N hydrochloric acid (12 ml) was further added to make the solution acidic. A white precipitate thereby deposited was filtrated, followed by washing with water and then drying to obtain 3.56 g of crude crystals of the subject (±)ACP acid derivative-B. To this crude crystals, benzene (15 ml) was added to dissolve them with heating, followed by cooling to room temperature. Crystals deposited were filtrated to give 3.06 g (11.7 mmol; yield: 78.0%) of the subject (±)ACP acid derivative-B (melting point: 126–131° C.).

Example 3

Optical resolution of (±)ACP acid derivative-B:

To methanol (60 ml), the (±)ACP acid derivative-B (3.90 g, 14.9 mmol) obtained in Reference Example 3 and a solution prepared by dissolving (−)-α-methylbenzylamine (1.80 g, 14.9 mmol) as an optically resolving agent in methanol (10 ml) were added. While these were heated and reacted, the solvent was evaporated to obtain a white precipitate. This white precipitate was further recrystallized eight times with 2-propanol. The diastereomer salt crystals thus obtained had the properties as shown below.

Melting point: 150–151° C. $[\alpha]_{589}$ 34.4° (c=1.052, methanol)

As a result, the diastereomer salt crystals obtained were found to be a [(+)ACP acid derivative-B.(−)optically resolving agent] salt.

To the crystals obtained, an aqueous 1N sodium hydroxide solution (5 ml) was added, and the optically resolving agent released was separated and removed by extraction with the addition of diethyl ether (15 ml). To the aqueous layer formed, 4N hydrochloric acid was added, and a white precipitate thereby deposited was filtrated to give 0.517 g (1.97 mmol) of (+)ACP acid derivative-B {(+)-cis-4-(N-carbobenzoxy)cyclopent-2-en-1-carboxylic acid}(yield: 26.6% based on (±)ACP acid derivative-B; $[\alpha]_{589}$ =34.0° (c=1.001, methanol).

The (+)ACP acid derivative-B thus obtained was allowed to react with optically active 1-(1naphthyl)ethylamine to derive its amido form, which was then analyzed by HPLC to reveal that it had an optical purity of 99% or more.

Conditions for HPLC
Column: Inertsil SIL (5 μm in diameter)
Mobile phase: n-Hexane/2-propanol=96/4
Flow rate: 1.0 ml/min.

What is claimed is:

1. A process for optically resolving a (±)-cis-4-aminocyclopent-2-en-1-carboxylic acid derivative represented by Formula (1):

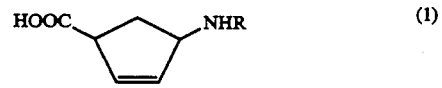

wherein R represents an acyl group; into its (+)-derivative and (−)-derivative, wherein the process comprises the step of allowing the (±)-cis-4-aminocyclopent-2-en-1-carboxylic acid derivative to react with an optically resolving agent comprising an optically active cis-2-(arylalkylamino)cyclohexanemethanol or an optically active α-alkylbenzylamine, to form diastereomer salts respectively corresponding to said (+)-derivative and said (−)-derivative.

2. The process according to claim 1, which further comprises the steps of separating said diastereomer salts respectively corresponding to said (+)-derivative and said (−)-derivative, subjecting the resulting respective diastereomer salts to alkali hydrolysis to release the optically resolving agent to remove it, and neutralizing the resulting alkali metal salt of said (+)-derivative or (−)-derivative with an acid to give the (+)-derivative or the (−) -derivative.

3. The process according to claim 1 or 2, wherein said optically resolving agent is used in an equivalent mole of from 0.4 to 1.0 based on the (±)-cis-4-aminocyclopent-2-en-1-carboxylic acid derivative.

4. The process according to any one of claims 1 to 3, wherein said optically resolving agent is cis-2-benzylaminocyclohexanemethanol or α-methylbenzylamine.

* * * * *

UNITED STATES PATENT AND TRADEMARK OFFICE
CERTIFICATE OF CORRECTION

PATENT NO. : 5,371,282
DATED : December 6, 1994
INVENTOR(S) : Hiroyuki NOHIRA, et al.

It is certified that error appears in the above-identified patent and that said Letters Patent is hereby corrected as shown below:

Column 3, line 25, "franoyl" should read –furanoyl–.
Column 5, line 25, "(+) ACP" should read –(±) ACP–.
Column 5, line 30, "(+) ACP" should read –(±) ACP–.

Signed and Sealed this

Sixteenth Day of December, 1997

*Attest:*

BRUCE LEHMAN

*Attesting Officer*   Commissioner of Patents and Trademarks